(12) United States Patent
Kinsella (10) Patent No.: US 7,872,096 B2
(45) Date of Patent: Jan. 18, 2011

(54) METHODS FOR CYCLIZING SYNTHETIC POLYMERS

(75) Inventor: Todd M. Kinsella, Redwood City, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 621 days.

(21) Appl. No.: 11/136,806

(22) Filed: May 24, 2005

(65) Prior Publication Data

US 2005/0282736 A1   Dec. 22, 2005

Related U.S. Application Data

(60) Provisional application No. 60/574,238, filed on May 24, 2004.

(51) Int. Cl.
*C07K 5/12* (2006.01)

(52) U.S. Cl. .......................... 530/317; 506/26; 506/43; 514/9

(58) Field of Classification Search ........................ None
See application file for complete search history.

(56) References Cited

U.S. PATENT DOCUMENTS

| | | | |
|---|---|---|---|
| 5,834,247 | A | 11/1998 | Comb |
| 6,184,344 | B1 | 2/2001 | Kent |
| 6,307,018 | B1 | 10/2001 | Kent |
| 6,326,468 | B1 | 12/2001 | Canne et al. |
| 6,455,247 | B1 | 9/2002 | Nolan |
| 6,562,617 | B1 | 5/2003 | Anderson |
| 2002/0150912 | A1 | 10/2002 | Owman |
| 2002/0151006 | A1 | 10/2002 | Muir |
| 2002/0192773 | A1 | 12/2002 | Walsh |
| 2003/0013148 | A1 | 1/2003 | Evans |
| 2003/0149234 | A1 | 8/2003 | Botti et al. |
| 2003/0166004 | A1* | 9/2003 | Gyuris et al. ................. 435/7.1 |
| 2004/0014100 | A1 | 1/2004 | Lorenz |

FOREIGN PATENT DOCUMENTS

| WO | WO 01/66565 A2 * | 9/2001 |
|---|---|---|
| WO | WO 03/027137 | 4/2003 |

OTHER PUBLICATIONS

Evans et al (1999 JBC 274:18359-18363).*
Wang et al (2002 JACS 124:1836-1837).*
Scott et al (1999 PNAS 96:13638-13643).*
Rose (1994 JACS 116:30-33).*
Liu et al (1994 PNAS 91:6584-6588).*
Schlolzer et al (1992 Science 256:221-225).*
Blaschke et al., Protein Engineering by Expressed Protein Ligation, Methods Enzymol., 328:478-496, 2000.
Camarero et al., Peptide Chemical Ligation Inside Living Cells: In Vivo Generation of a Circular Protein Domain, Boorganic & Medicinal Chem., 9: 2479-2484, 2001.
Dawson et al., Synthesis of Native Proteins by Chemical Ligation, Annu. Rev. Biochem, 2000, 69:923-60.
Derbyshire et al., Lightning Strikes Twice: Intron-Entein Coincidence, Proc. Natl. Acad. Sci., 1998, 95:1356-1357.
Hackeng et al., Protein Synthesis by Native Chemical Ligation: Expanded Scope by Using Straightforward Methodology, Proc. Natl. Acad. Sci., 1999, 96: 10068-10073.
Kinsella et al., Retrovirally Delivered Random Cyclic Peptide Libraries Yield Inhibitors of Interleukin-4 Signaling in Human B Cells, J. Biol. Chem., 2002, 277:37512-8.
Lew et al., Characteristics of Protein Splicing in Trans Mediated by a Semisynthetic Split Intein, 1999, Biopoly, 51: 355-362.
Muir et al., Expressed Protein Ligation: A General Method for Protein Engineering, Proc. Natl. Acad. Sci., 1998, 95:6705-6710.
Wu et al., Protein Trans-Splicing by a Splite Intein Encoded in a Split DNAE Gene of *Synechocystis* SP. PCC6803, Proc. Natl. Acad. Sci., 1998, 95:9226-9231.

* cited by examiner

*Primary Examiner*—Amber D. Steele
*Assistant Examiner*—Christopher M Gross
(74) *Attorney, Agent, or Firm*—James S. Keddie; Carol L. Francis; Travis Young (57) ABSTRACT

The invention provides methods and compositions for production of a cyclic polymer in a cell free system. In general, the methods of the invention involve ligating first and second recombinant intein domains to a linear synthetic polymer to form a compound containing the structure: $D_1$-$X_{(n)}$-$D_2$, where $D_1$ is a first catalytic domain of an intein; $D_2$ is a second catalytic domain of an intein; where the second catalytic domain has at its N-terminus a first reactive site for the intein; and $X_{(n)}$ is a polymer of a number n of monomer X, where the polymer N-terminus has a second reactive site for the intein. $D_1$-$X_{(n)}$-$D_2$ compounds autocatalytically cyclize the $X_{(n)}$ polymer to produce a cyclic polymer. The invention finds use in a variety of drug discovery, clinical and therapeutic applications.

12 Claims, 7 Drawing Sheets

Step 3 Cleavage of IntB-peptide from column releasing activated thioester

FIG. 3D

Step 4  Ligation of IntA to IntB-peptide via attck of activated thioester, followed by spontaneous S-N acyl rearrangement to yeild a reconstituted intein complex containing a central synthetic peptide substrate.

FIG. 3E

Step 5  Incubation at 25°C initiates intein catalysis and generates the cyclic peptide end-product

METHODS FOR CYCLIZING SYNTHETIC POLYMERS

FIELD OF THE INVENTION

The present invention generally relates to methods and compositions for cyclizing synthetic polymers, e.g., synthetic peptides.

BACKGROUND OF THE INVENTION

Cyclic peptides are conformationally restricted and, as such, exhibit increased specificity and affinity in binding to other molecules, as compared to linear peptides. Further, cyclic peptides are thought to be more stable in cells and on the shelf than linear peptides, and may be small enough to avoid recognition by host immune system and to cross the plasma membrane of a cell (Schreiber, 2000 Science 287, 1964-1969; Scott et al., 2001 Chem. Biol. 8, 801-815).

These features make cyclic peptides very attractive drugs. Accordingly, there is a great need for new methods for making cyclic peptides, particularly for the manufacture of synthetic cyclic peptides for clinical investigations and therapeutic use, and for the production of cyclic peptide libraries that can be screened to identify cyclic peptides with a desired activity.

Current methods for making cyclic peptides, however, generally fail to meet this need. For example, linear peptides may be cyclized in vitro by reacting the N- and C-termini of a peptide together to form a covalent bond, e.g., a peptide bond, therebetween. Such methods are typically inefficient because the ends of a peptide are sterically prevented from reacting. This problem is particularly exacerbated in cyclizing smaller peptides, where the ends of the peptide have less choice of conformational space. Further, cyclic peptides made by cyclizing linear peptides can be difficult to purify from the linear peptides, and, as such, such methods sometimes require sophisticated purification procedures. Accordingly, it is often difficult to produce and purify a cyclic peptide in any useful amount using synthetic chemistry.

Further, while inteins have been used to cyclize peptides in vitro and in vivo, those peptides are typically synthesized in vivo, i.e., by ribosomes in a cell. Such cyclic peptides therefore typically contain only genetically-encodable amino acids (i.e., L-amino acids) and, as such, are limited in their structural diversity. Further, before their use, cyclic peptides produced in a cell are typically purified away from other cellular components before use. Since this is not a trivial task, cyclic peptides made by cells cannot generally be produced in large amounts, are typically not amenable to typical high throughput, cell-free, screening assays, and may not be suitable for many clinical studies. In addition, cell-based methods are limited to production of cyclic polymers that are genetically encodable.

Accordingly, there is still a great need for new methods for producing cyclic peptides. In particular, there is a great need for cell-free system methods of producing small cyclic peptides containing non-genetically encodable amino acids.

This invention meets this need, and others.

Literature

Dawson et al. (Annu. Rev. Biochem 2000 69:923-60); Arnold et al. (Scientific World Journal 2001 1:117); Blaschke et al. (Methods Enzymol. 328:478-496); Wu et al. (Proc. Natl. Acad. Sci. 1998 95:9226-9231); Derbyshire et al. (Proc. Natl. Acad. Sci. 1998 95:1356-1357); Kinsella et al. (J. Biol. Chem. 2002 277:37512-8) and Muir et al. (Proc. Natl. Acad. Sci. 1998 95:6705-6710); Published U.S. Patent Applications 20020151006, 20030013148, 20040014100, 20020192773 and 20020150912; and U.S. Pat. Nos. 5,834,247, 6,307,018, 6,184,344, 6,562,617 and 6,455,247.

SUMMARY OF THE INVENTION

The invention provides methods and compositions for production of a cyclic polymer in a cell free system. In general, the methods of the invention involve ligating first and second recombinant intein domains to a linear synthetic polymer to form a compound containing the structure: $D_1$-$X_{(n)}$-$D_2$, where $D_1$ is a first catalytic domain of an intein, $D_2$ is a second catalytic domain of an intein, the second catalytic domain has at its N-terminus a first reactive site for the intein and $X_{(n)}$ is a polymer of a number n of monomer X, where the polymer N-terminus has a second reactive site for the intein. $D_1$-$X_{(n)}$-$D_2$ compounds autocatalytically cyclize the $X_{(n)}$ polymer to produce a cyclic polymer. Libraries of $D_1$-$X_{(n)}$-$D_2$ compounds can be used in production of libraries of cyclic polymers. The invention finds use in a variety of drug discovery, clinical and therapeutic applications.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DEFINITIONS

Before the present invention is further described, it is to be understood that this invention is not limited to particular embodiments described, as such may of course vary. It is also to be understood that the terminology used herein is for the purpose of describing particular embodiments only, and is not intended to be limiting. Unless defined otherwise, all technical and scientific terms used herein have the same meaning as commonly understood by one of ordinary skill in the art to which this invention belongs.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Throughout this application, various publications, patents and published patent applications are cited. The disclosures of these publications, patents and published patent applications referenced in this application are hereby incorporated by reference in their entirety into the present disclosure. Citation herein by Applicant of a publication, patent, or published patent application is not an admission by Applicant of said publication, patent, or published patent application as prior art.

It must be noted that as used herein and in the appended claims, the singular forms "a", "and", and "the" include plural referents unless the context clearly dictates otherwise. Thus, for example, reference to "a polypeptide" includes a plurality of such polypeptides, and reference to "the compound" includes reference to one or more compounds and equivalents thereof known to those skilled in the art, and so forth. It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The term "polymer", as used herein, refers to a linear or cyclic compound that is made up of a series of monomers or subunits that are covalently bonded together to form a chain. A polymer may be a homopolymeric (i.e., may contain monomers that are identical to each other) or may be a heteropolymeric (i.e., may contain monomers that are different to each other). A polymer may therefore contain two or more different monomers (i.e., monomers that have chemical structures that are different to each other). In certain embodiments the monomers of a polymer are below about 500 Da in size (e.g., about 50 Da to about 150 Da in size).

The term "organic polymer", as used herein, refers to a polymer that primarily contains atoms of carbon (C) and hydrogen (H). Organic polymers are generally made up of any combination of carbon, nitrogen, oxygen and hydrogen atoms, for example. Exemplary organic polymers include plastics (e.g., poly(vinyl chloride), polyacrylate, polyethylene, polypropylene, poly(4-methylbutene), polystyrene, polymethacrylate, poly(ethylene terephthalate), nylon, poly (vinyl butyrate) and epoxy) and biopolymers, e.g., polypeptides (as discussed below), nucleic acids, carbohydrates (e.g., cellulose polymers such as nitrocellulose, cellulose acetate, dextran and agarose, etc.), lipids, and molecules containing any mixture of amino acids, nucleotides, sugar or lipid monomers. The chemistry for making organic polymers is generally well known in the art.

A "biopolymer" is a polymer containing amino acid and/or nucleotide monomers, regardless of its source. A biopolymer may be naturally-occurring, obtained from a cell-based recombinant expression system, or synthetic. The term "biopolymer" refers to polypeptides and polynucleotides and includes compounds containing amino acids, nucleotides, or a mixture thereof.

The terms "polypeptide" and "protein" are used interchangeably throughout the application and mean at least two covalently attached amino acids, which includes proteins, polypeptides, oligopeptides and peptides. A polypeptide may be made up of naturally occurring amino acids and peptide bonds, synthetic peptidomimetic structures, or a mixture thereof. Thus "amino acid", or "peptide residue", as used herein encompasses both naturally occurring and synthetic amino acids and includes optical isomers of naturally occurring (genetically encodable) amino acids, as well as analogs thereof. For example, homo-phenylalanine, citrulline and noreleucine are considered amino acids for the purposes of the invention. "Amino acid" also includes imino acid residues such as proline and hydroxyproline. The side chains may be in either the D- or the L-configuration. If non-naturally occurring side chains are used, non-amino acid substituents may be used, for example to prevent or retard in vivo degradation. The term "amino acid" encompasses $\alpha$- and $\beta$-amino acids.

In general, polypeptides may be of any length, e.g., greater than 2 amino acids, greater than 4 amino acids, greater than about 10 amino acids, greater than about 20 amino acids, greater than about 50 amino acids, greater than about 100 amino acids, greater than about 300 amino acids, usually up to about 500 or 1000 or more amino acids. "Peptides" are generally greater than 2 amino acids, greater than 4 amino acids, greater than about 10 amino acids, greater than about 20 amino acids, usually up to about 10, 20, 30, 40 or 50 amino acids. In certain embodiments, peptides are between, 3 and 5 or 5 and 30 amino acids in length. In certain embodiments, a peptide may be three or four amino acids in length.

The term "fusion protein" or grammatical equivalents thereof is meant a protein composed of a plurality of polypeptide components that while typically unjoined in their native state, typically are joined by their respective amino and carboxyl termini through a peptide linkage to form a single continuous polypeptide. Fusion proteins may be a combination of two, three or even four or more different proteins. The term polypeptide includes fusion proteins, including, but not limited to, a fusion of two or more heterologous amino acid sequences, a fusion of a polypeptide with: a heterologous targeting sequence, a linker, an immunologically tag, a detectable fusion partner, such as a fluorescent protein, $\beta$-galactosidase, luciferase, etc., and the like.

The terms "nucleic acid molecule" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular and may contain modifications in the backbone to increase stability and half life of such molecules in physiological environments.

The nucleic acid may be double stranded, single stranded, or contain portions of both double stranded or single stranded sequence. As will be appreciated by those in the art, the depiction of a single strand ("Watson") also defines the sequence of the other strand ("Crick").

By the term "recombinant nucleic acid" herein is meant nucleic acid not normally found in nature. In general, a "recombinant nucleic acid" is originally constructed in vitro, e.g., by the manipulation of nucleic acid by endonucleases. Thus an isolated nucleic acid in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, e.g., using the in vivo cellular machinery of the host cell rather than in vitro manipulations. However, such nucleic acids, once produced recombinantly, although subsequently replicated non-recombinantly, are still considered recombinant for the purposes of the invention.

The term "endogenous", when used in reference to a biopolymer, means that which is naturally produced (e.g., by an unmodified mammalian or human cell). As used herein, the terms "endogenous" and "native" are interchangeable.

A "deletion" is defined as a change in the sequence of a biopolymer in which one or more residues are absent as compared to a sequence of a parental biopolymer. A deletion can remove about 2, about 5, about 10, up to about 20, up to about 30 or up to about 50 or more amino acids. A biopolymer may contain more than one deletion.

An "insertion" or "addition" is a change in a sequence of a biopolymer that results in the addition of one or more residues, as compared to a sequence of a parental biopolymer. "Insertion" generally refers to addition to one or more residues within a biopolymer, while "addition" can be an insertion or refer to amino acid residues added at an end, or both termini, of a biopolymer. An insertion or addition is usually of about 1, about 3, about 5, about 10, up to about 20, up to about 30 or up to about 50 or more amino acids. A biopolymer may contain more than one insertion or addition.

A "substitution" results from the replacement of one or more residues of a biopolymer by different residues, as compared to a sequence of a parental biopolymer. It is understood that a polypeptide may have conservative amino acid substitutions which have substantially no effect on activity of the polypeptide. By conservative substitutions is intended combinations such as gly, ala; val, ile, leu; asp, glu; asn, gln; ser, thr; lys, arg; and phe, tyr.

The term "assessing" includes any form of measurement, and includes determining if an element is present or not. The terms "determining", "measuring", "evaluating", "assessing" and "assaying" are used interchangeably and includes quantitative and qualitative determinations. Assessing may be relative or absolute. "Assessing the presence of" includes determining the amount of something present, and/or determining whether it is present or absent.

As used herein the term "isolated," when used in the context of an isolated compound, refers to a compound of interest that is in an environment different from that in which the compound naturally occurs. "Isolated" is meant to include compounds that are within samples that are substantially enriched for the compound of interest and/or in which the compound of interest is partially or substantially purified.

The term "isolated" also means that the recited material is usually unaccompanied by at least some of the material with which it is normally associated in its natural state, preferably constituting at least about 0.5%, more preferably at least about 5% by weight of the total protein in a given sample. "Purified" means that the recited material comprises at least about 75% by weight of the total protein, with at least about 80% being preferred, and at least about 90% being particularly preferred.

As used herein, the term "substantially pure" refers to a compound that is removed from its natural environment and is at least 60% free, preferably at least 75% free, and most preferably at least 90% free from other components with which it is naturally associated.

A "coding sequence" or a sequence that "encodes" a selected polypeptide, is a nucleic acid molecule which can be transcribed (in the case of DNA) and translated (in the case of mRNA) into a polypeptide, for example, in a host cell when placed under the control of appropriate regulatory sequences (or "control elements"). The boundaries of the coding sequence are typically determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral or prokaryotic DNA, and synthetic DNA sequences. A transcription termination sequence may be located 3' to the coding sequence. Other "control elements" may also be associated with a coding sequence. A DNA sequence encoding a polypeptide can be optimized for expression in a selected cell by using the codons preferred by the selected cell to represent the DNA copy of the desired polypeptide coding sequence.

"Operably linked" refers to an arrangement of elements wherein the components so described are configured so as to perform their usual function or a function of interest. In the case of a promoter, a promoter that is operably linked to a coding sequence will effect the expression of a coding sequence. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence. In the context of a $D_1$-$X_{(n)}$-$D_2$ compound of the invention, the elements of the compound are operably linked so as to provide for autocatalytic cyclization and production of a cyclic polymer of interest.

By "nucleic acid construct" is meant a nucleic acid sequence that has been constructed to comprise one or more functional units not found together in nature. Examples include circular, linear and double-stranded nucleic acids, extrachromosomal DNA molecules (plasmids), cosmids (plasmids containing COS sequences from lambda phage), viral genomes comprising non-native nucleic acid sequences, and the like.

A "vector" is capable of transferring nucleic acids into to a host cell. Typically, "vector construct," "expression vector," and "gene transfer vector," mean any nucleic acid construct capable of directing the expression of a nucleic acid of interest and which can transfer nucleic acid sequences to host cells. This can be accomplished by genomic integration of all or a portion of the vector, or transient or inheritable maintenance of the vector as an extrachromosomal element. Thus, the term includes cloning and expression vehicles, as well as integrating vectors.

An "expression cassette" encompasses any nucleic acid for directing expression of a coding sequence of interest. In most embodiments, express cassettes contain a coding sequence operably linked to an expression-regulatory sequence, e.g., a promoter. Such cassettes can be constructed in a vector in order to transfer the expression cassette into a host cell.

A polynucleotide is "derived from" a particular cell if the polynucleotide was obtained from the cell. A polynucleotide may also be "derived from" a particular cell if the polynucleotide was obtained from the progeny of the cell, as long as the polynucleotide was present in the original cell. As such, a single cell may be isolated and cultured, e.g., in vitro, to form a cell culture prior to isolating a nucleic acid from that cell.

The terms "conformationally restrained" and "conformationally restricted" are used interchangeable herein to describe a compound (usually a polypeptide) that contains covalent or non-covalent bonds between units (i.e., intramolecular bonds) (e.g., as between amino acids within a polypeptide) and is restricted in its conformation. For example, amino acids within a conformationally restrained polypeptide are generable not able to freely rotate around their peptide bonds. Conformationally restrained polypeptides, and methods for making conformationally restrained polypeptides, are generally well known in the art (see, e.g., U.S. Pat. No. 6,596,485).

A "cyclic polypeptide" is a type of conformationally restrained polypeptide that, as its name suggests, contains a cyclic polymer of amino acids. The term "cyclic polypeptide" is used to describe a polypeptide (including a cyclic peptide) that is circularized via a peptide bond between the N and C terminal amino acids of a linear polypeptide (as described in U.S. published patent application 20040014100, for example).

Each monomer of a cyclic polypeptide may comprise an amino acid, where an "amino acid", as discussed above, refers to a natural amino acid (i.e., a genetically coded amino acid residue), a non-natural amino acid (for example, a non-genetically coded amino acid residue) such as an analog of a natural amino acid or a modified amino acid (for example, an amino acid that has been conjugated to an unrelated moiety, for example, PEG). Thus, a cyclic peptide may be a polymer of monomeric units that are: (a) natural amino acid residues; (b) non-natural amino acid residues; or (c) both natural and non-natural amino acid residues, which monomeric units are covalently joined. The term "cyclic peptide" includes synthetic peptides and peptides made by a cell. Amino acids are sometimes referred to herein by standard one- or three-letter symbols (see, for example, pages 58-59, "Biochemistry" Second Ed., Voet and Voet, eds. (1995) John Wiley & Sons, Inc.). As used herein, and unless specifically indicated otherwise, those symbols refer to natural amino acids as well as non-natural analogs of those non-natural amino acids. In presenting the amino acid sequence of a cyclic peptide using a linear string of one- or three-letter symbols, it is understood that the first and last amino acids of the string are covalently joined together. Since such a molecule is circular, a cyclic peptide amino acid sequence can be written starting at any point of the sequence. For example, a cyclic peptide having the amino acid sequence "SAW" is identical to a cyclic peptide having the sequence "AWS" or "WSA". Alternatively, cyclic peptides can be referred to as "cyclo[$X_1X_2X_3$]," where $X_1$, $X_2$ and $X_3$ are amino acids. For example, the terms "cyclo [SAW]", "cyclo[AWS]" and "cyclo[WSA]" refer to the same cyclic peptide. Sometimes "cyclo" will be replaced by shorthand "c" for example, "cyclo[SAW]" may be designated "c[SAW]."

The term "test polypeptide" is a polypeptide to be tested for biological activity in an assay. At the time of testing, a test polypeptide may have known or unknown sequence.

The term "randomized amino acid sequence" refers to a polypeptide having an amino acid sequence that is at least partially randomized, including fully randomized. When made recombinantly, a library of polypeptides having randomized amino acid sequences usually contains polypeptides having any of the naturally occurring amino acids, or any subset thereof, present into at least one or all positions (e.g., at last 1, 2, 3, 4, 5, about 8, about 10, about 15, about 20, usually up to at least 100 or more positions) of the polypeptide. Polypeptides having a randomized amino acid sequence are usually produced using synthetic nucleic acids that contain any of the four nucleotides, or a subset thereof, in at least one or all positions of the polynucleotide.

The term "specific binding" refers to the ability of a polypeptide to preferentially bind to a binding partner for that polypeptide that is present in a homogeneous mixture of different analytes. Typically, a specific binding interaction will discriminate between binding partners for a polypeptide and other analytes by more than about 10 to 100-fold or more (e.g., more than about 1000- or 10,000-fold). Typically, the affinity between a particular polypeptide and binding partner for the polypeptide when they are specifically bound in a polypeptide/binding partner complex is characterized by a $K_D$ (dissociation constant) of at least $10^{-6}$ M, at least $10^{-7}$ M, at least $11^{-8}$ M, at least $10^{-9}$ M, usually up to about $10^{-10}$ M.

The term "polypeptide/binding partner complex" is a complex that results from the specific binding of a polypeptide to a binding partner for the polypeptide, i.e., a "binding partner pair". A polypeptide and a binding partner for the polypeptide will typically specifically bind to each other under "conditions suitable for specific binding", where such conditions are those conditions (in terms of salt concentration, pH, detergent, protein concentration, temperature, etc.) which allow for binding to occur between the members of a binding partner pair in solution. Such conditions, particularly with respect to receptors and ligands, are well known in the art. Conditions suitable for specific binding typically permit specific binding of a polypeptide to a binding partner with a dissociation constant ($K_D$) of less than about $10^{-6}$ M to each other, but not to other analytes.

A "library" of cells is a plurality of cells. Such a library may be a mixture of different cells, or may contain cells that are separated from each other (e.g., in the wells of a multi-well plate).

The terms "pool" or "mixture", as used herein, refers to a combination of elements, e.g., cells or polypeptides, that are interspersed in two or three dimensions and not in any particular order. A mixture is homogeneous and not spatially separable into its different constituents. Examples of mixtures of elements include a number of different polypeptides that are present in the same solution (e.g., an aqueous solution). In other words, a mixture is not addressable. To be specific, an arrayed library of polypeptides, as is commonly known in the art, is not a mixture of polypeptides because the elements of the library are spatially distinct and the array is addressable.

The terms "treatment", "treating", "treat", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease and/or relieving one or more disease symptoms. "Treatment" is also meant to encompass delivery of an agent in order to provide for a pharmacologic effect, even in the absence of a disease or condition. For example, "treatment" encompasses delivery of a receptor modulator that can provide for enhanced or desirable effects in the subject (e.g., reduction of pathogen load, beneficial increase in a physiological parameter of the subject, reduction of disease symptoms, etc.).

"Subject", "individual," "host" and "patient" are used interchangeably herein, to refer to an animal, human or non-human, susceptible to or having a receptor-related disorder amenable to therapy according to the methods of the invention. Generally, the subject is a mammalian subject. Exemplary subjects include, but are not necessarily limited to, humans, non-human primates, mice, rats, cattle, sheep, goats, pigs, dogs, cats, and horses, with humans being of particular interest.

Other definitions of terms appear throughout the specification.

DETAILED DESCRIPTION OF THE INVENTION

The invention provides methods for making compositions that are useful for producing cyclic polymers, e.g., cyclic peptides, using a cell free system. In general, the method involves ligating first and second recombinant intein domains to a linear synthetic polymer to form a compound containing the structure: $D_1$-$X_{(n)}$-$D_2$, where $D_1$ is a first catalytic domain of an intein, $D_2$ is a second catalytic domain of an intein, wherein the second catalytic domain has at its N-terminus a first reactive site for the intein, and $X_{(n)}$ is a polymer composed of n units of monomer X, wherein the polymer has a second reactive site for the intein at its N-terminus. A subject compound can autocatalytically cyclize the $X_{(n)}$ polymer that is part of the compound to produce a cyclic version of the polymer. Also described are libraries of such compounds for producing libraries of cyclic polymers. Methods of making cyclic polymers by incubating the subject compounds are also provided. The invention finds use in a variety of drug discovery, clinical and therapeutic applications.

In further describing the invention in greater detail than provided in the Summary and as informed by the Background and Definitions provided above, the subject compositions and methods for making cyclic polymers will be described first, followed by a discussion of the compositions produced by the subject methods. This discussion is followed by a review of representative applications in which the subject methods and compositions find use.

Compositions and Methods for Making Cyclic Polymers

Figure 1:
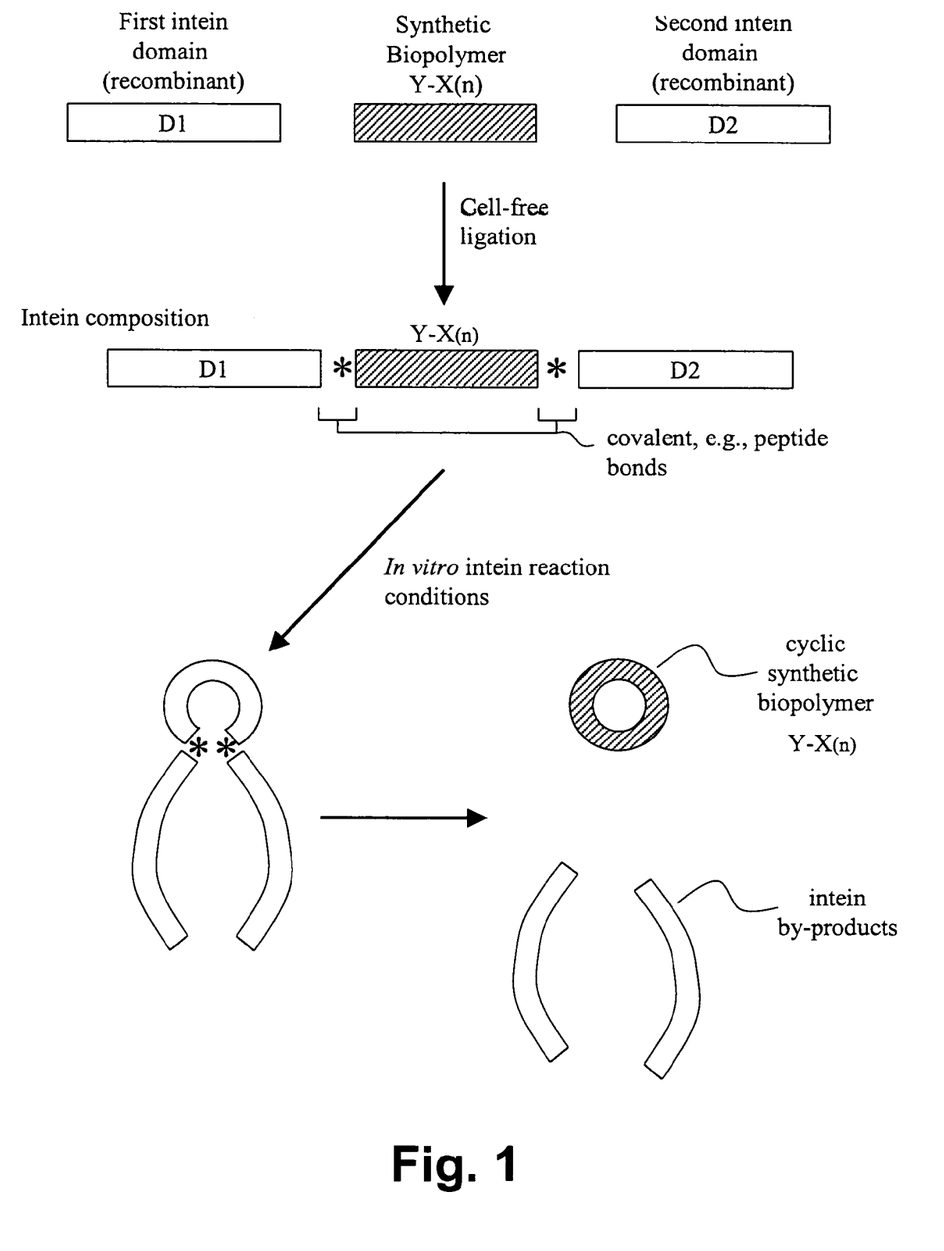
FIG. 1 is a first schematic representation of an embodiment of the invention.

As mentioned above, the invention provides an in vitro, i.e., cell-free, method for cyclizing a linear polymer. In general terms, the method involves two steps: an in vitro ligation step and an in vitro intein reaction step. The general features of the method are schematically illustrated in FIG. 1. Typically, and with reference to FIG. 1, two domains of an intein (i.e., first and second catalytic intein domains D1 and D2) are ligated to a synthetic polymer of monomer sequence $X_{(n)}$, to produce a recombinant intein composition of the formula D1-$X_{(n)}$-D2, where "—" is a covalent bond, typically a peptide bond. This recombinant composition, when subjected to suitable in vitro intein reaction conditions, autocatalyzes cyclization of the linear polymer to produce a cyclic polymer comprising the sequence $X_{(n)}$. Accordingly, the invention may be used to produce a cyclic polymer having a monomer sequence $X_{(n)}$ from a linear polymer containing the same sequence as the cyclic polymer.

From this point forward, an intein/polymer composition having the formula D1-$X_{(n)}$-D2, as described above, will be referred to as an "intein composition".

In further describing these methods, the subject inteins and polymers will be described first, followed by a review of methods by which they may be ligated together to produce a linear intein composition. Methods for producing cyclic polymers using an intein composition are then described.

Inteins

The inteins that may be used in the subject methods are capable of protein splicing in trans or cis. Such inteins are well known in the art and are reviewed in a number of publications, including Paulus (Annual Review of Biochemistry, 2000, 69: 447-496), Paulus (Chemical Society Reviews 1998 27:375-386), Paulus (Bioorganic Chemistry 2001 29:119-129) and published U.S. patent applications 20040014100 and 20030013148. A comprehensive list of inteins and description of their biology may be found at New England Biolabs Intein Database (InBase Reference: Perler, F. B. (2002). InBase, the Intein Database. Nucleic Acids Res. 30, 383-384), as found at the world wide website of New England Biolabs.

Inteins of any origin (i.e., naturally occurring inteins or catalytically active naturally occurring or man-made variants thereof) may be employed in the methods described herein. An intein may be of bacterial, yeast, mammalian or viral origin, for example. Accordingly and without wishing to limit the invention to any particular intein, exemplary inteins for use in the subject methods include: the Ssp DnaB intein from *Synechocystis* spp. strain PCC6803, the Mxe GyrA intein from *Mycobacterium xenopi*, the CIV RIR1 intein from *Chilo iridescent virus*, the Ctr VMA intein from *Candida tropicalis*, the Gth DnaB intein from *Guillardia theta*, the Ppu DnaB intein from *Porphyra purpurea*, the Sce VMA intein from *Saccharomyces cerevisiae*, the Mfl RecA intein from *Mycobacterium flavescens*, the Ssp DnaE intein from *Synechocystis* spp. strain PCC6803, the Mle DnaB intein from *Mycobacterium leprae*, the Mja KlbA intein from *Methanococcus jannaschii*, the Pfu KlbA from *Pyrococcus furiosus*, the Mth RIR1 intein from *Methanobacterium thermoautotrophicum* (delta H strain), the Pfu RIR1-1 intein from *Pyrococcus furiosus*, the Psp-GBD Pol intein from *Pyrococcus* spp. the GB-D, Thy Pol-2 intein from *Thermococcus hydrothermalis*, the Pfu IF2 intein from *Pyrococcus furiosus*, Pho Lon intein from *Pyrococcus horikoshii* OT3, the Mja r-Gyr intein from *Methanococcus jannaschii*, the Pho RFC intein from *Pyrococcus horikoshii* OT3, the Pab RFC-2 intein from *Pyrococcus abyssi*, the Mja RtcB (Mja Hyp-2) intein from *Methanococcus jannaschii*, the Pho VMA intein from *Pyrococcus horikoshii* OT3, the Mtu RecA intein, the PI-pfuI intein and the PU-pfu II intein, and artificial trans-splicing variants thereof.

As is well recognized in the art, inteins typically are composed of two domains (termed herein the "N-terminal domain" and "C-terminal domain") that can be naturally (in the case of the Ssp DnaE intein, for example) or non-naturally (i.e., artificially or by recombinant means, for example) present as two different molecules. These intein domains, when present together, can reconstitute an active intein, and can be used to join two different polypeptides together in trans or in cis. Also as well recognized in the art, inteins may be used to produce cyclic peptides in vivo and in vitro. Such methods are generally described in published U.S. patent application 20040014100, Camarero and Muir (J. Am. Chem. Soc. 1999 121:5597-5598), Iwai and Pluckthun (FEBS Lett. 1999 459:166-172), Evans, et al. (J. Biol. Chem. 1999 274: 18359-18363) and Scott et al. (Proc. Natl. Acad. Sci. 1999 96:13638-13643). Any intein may be used to make a cyclic peptide.

As mentioned above, the N- and C-terminal domains of an intein may be used to effect splicing in cis or in trans. Since those domains will be used in the methods described herein in cis (i.e., as part of the same molecule), but in a different order in which they may naturally occur, the C- and N-terminal intein domains, as used in an intein composition described in great detail below, will be referred to herein as first and second intein catalytic domains, respectively. In other words, as is well known in the art, an intein typically consists of two intein domains, i.e., an N-terminal domain and a C-terminal domain, that together can auto-catalyze an intein-mediated splicing reaction in cis or in trans. Since the intein compositions described herein typically contain an N-terminal intein domain at the C-terminal end of the composition, and a C-terminal intein domain at the N-terminal end of the composition, the C- and N-terminal domains of an intein are herein termed first and second catalytic intein domains, respectively. In particular embodiments, the first and second catalytic intein domains may be referred to as "D1" (or "$D_1$") and "D2" (or "$D_2$"), respectively. Accordingly, the first and second catalytic intein domains referred to herein correspond to the C- and N-terminal domains of a so called "split" intein (i.e., an naturally or artificially split intein) which, together, can effect a protein splicing reaction. The relationship between the described N- and C-terminal intein domains and the first and second catalytic intein domains used in the instant methods is described in FIG. 2.

Naturally-occurring intein-mediated protein splicing proceeds according to one of two pathways, a classical and alternative pathway depending on which particular intein is used. Naturally-occurring inteins that catalyze splicing using the classical pathway, such as many of those listed above, typically contain a N-terminal cys or ser amino acid as an intein reactive site. Naturally-occurring inteins that catalyze splicing using the alternative pathway, such as the *M. jannaschii* KibA intein, and others, typically use a N-terminal ala amino acid as an intein reactive site. Almost all naturally-occurring inteins contain a ser, cys or thr amino acid as a C-terminal intein reactive site. Accordingly, in performing the subject methods, a wide variety of amino acids may be chosen for use at intein-reactive sites.

Since the N-terminal amino acid of an N-terminal domain of an intein may contains an intein reactive amino acid containing a hydroxyl (OH) or thiol (SH) group (e.g., a cys or ser or analog thereof), or ala or analog thereof, so too does the N-terminal amino acid of the second intein domain ($D_2$) typically used in the subject methods. Furthermore, since the C-terminal domain of an intein typically, but not always, ends its C-terminus in the his-asn dimer, so, too, do many of the first catalytic intein domains ($D_1$) used in the subject methods. As would be recognized by one of skill in the art, there is considerable flexibility at the "his-asn" position, and, accordingly other amino acid dimers, e.g., gly-asn, gly-gln, ser-asn, ala-asn, phe-asn, lys-asn, etc., or analogs thereof, may be present at this position instead of his-asn. The relationship between the described intein domains, the first and second catalytic intein domains used in the instant methods, and the various groups and dimer motifs discussed above, is described in FIG. 2.

An intein domain used in the present invention may be produced and/or used as a fusion protein, particularly as a fusion protein containing an affinity tag that can aid in purification of the protein and/or separation of the protein from other compounds (e.g., cyclic peptide products). Suitable affinity tags include any amino acid sequence that may be specifically bound to another moiety, usually another polypeptide, most usually an antibody. Suitable affinity tags include epitope tags, for example, the V5 tag, the FLAG tag, the HA tag (from hemagglutinin influenza virus), the myc tag, and the like, as is known in the art. Suitable affinity tags also include domains for which, binding substrates are known, e.g., HIS, GST and MBP tags, as is known in the art, and domains from other proteins for which specific binding partners, e.g., antibodies, particularly monoclonal antibodies, are available. Suitable affinity tags also include any protein-protein interaction domain, such as a IgG Fc region, which may be specifically bound and detected using a suitable binding partner, e.g. the IgG Fc receptor.

Prior to their ligation to a polymer, the subject first and second catalytic intein domains are typically produced using recombinant means, and purified. Methods for producing and isolating polypeptides are well known in the art (Ausubel, et al, Short Protocols in Molecular Biology, 5th ed., Wiley & Sons, 2002; Sambrook, et al., Molecular Cloning: A Laboratory Manual, Third Edition, (2001) Cold Spring Harbor, N.Y.) and need not be discussed in any more detail than that set forth above. In certain embodiments, an intein domain may be produced by cleavage of a larger protein, e.g., a mutant or wild type intein, with a cleavage agent, e.g., a thiol-containing agent or the like, for example, MESN, thiophenol or the like, to produce the intein domain. In particular embodiments, a variant form of an intein that is defective in completion of the splicing reaction but still capable of thioester intermediate formation may be cleaved to generate a first or second catalytic intein domain. Such inteins may be used to produce a intein domain containing a reactive thioester group, and are well known in the art (e.g., Xu et al. EMBO J. 1996 15: 5146-5153; Chong et al. Gene 1997 192:271-281). Such an intein, and a cleavage reaction producing a first catalytic intein domain, is exemplified in FIG. 3A.

Polymers of Interest

Any type of polymer may be cyclized using the subject methods, including organic polymers such as biopolymers that contain amino acid or nucleotide monomers, or a mixture of different types of monomers. Accordingly, polypeptides, polynucleotides, or a polymer containing both amino acid and nucleotide monomers, for example, may be cyclized using the subject methods. In many embodiments of the invention, the polymer used is a biopolymer containing amino acids, i.e., a polypeptide. Polymers that may be employed in the subject methods may not contain any peptide bonds. However, in certain embodiments, the polymers may contain peptide bonds in between the first and second monomers of one or both ends of the polymer to be cyclized. In certain embodiments, the subject polymers may contain thioester bonds, for example, between the first and second monomers of one or both ends of the polymer to be cyclized.

A polymer for use as a component $X_{(n)}$ of subject $D_1$-$X_{(n)}$-$D_2$ compounds may be made in a cell, e.g., by recombinant means, or synthetically (i.e., using a cell-free system, e.g., by employing a machine or in solution). Biopolymers used in the subject methods are generally synthetic biopolymers, and may be non-naturally occurring, may contain non-naturally occurring monomers, may contain a mixture of naturally occurring and non-naturally occurring monomers, and may not be genetically encodable, i.e., cannot be made in a cell. In certain embodiments, a synthetic biopolymer may contain only naturally occurring monomers, and, as such, may be identical to a naturally-occurring form or naturally produced form of the biopolymer. Methods for making synthetic biopolymers, e.g., synthetic polypeptides, are well known in the art and do not need to be described here in any great detail.

For example, biopolymers, e.g., polypeptides, can be produced by chemical synthesis, for example, by the solid phase peptide synthesis method of Merrifield et al. (J. Am. Chem. Soc. 1964 85:2149). Standard solution methods may also be used (see, for example, Bodanszky, Principles of Peptide Synthesis, Springer-Verlag, Berlin (1984) and Bodanszky, Peptide Chemistry, Springer-Verlag, Berlin (1993)). Subject biopolymers can be chemically synthesized by the methods of Creighton (1983, Proteins: Structures and Molecular Principles, W.H. Freeman & Co., N.Y.) or Hunkapiller et al. (Nature, 310:105-111 (1984)).

Biopolymers may be produced using a biopolymer synthesizer (e.g. a peptide synthesizer of Applied Biosystems, Foster City, Calif.). Furthermore, if desired, non-naturally amino acids or chemical amino acid analogs can be introduced into a polypeptide sequence. Non-classical amino acids include non-genetically encodable amino acids (i.e., amino acids that cannot be produced and used to make protein in a cell using ribosomes), such as the D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, 5 hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acids can be D (dextrorotary) or L (levorotary). Further methods and amino acid analogs for peptide synthesis may be found in Chan et al, (Fmoc solid phase peptide synthesis: A Practical Approach, Oxford University Press, 2000) and Bodanszky (Principles of Peptide Synthesis, Springer Verlag, 2nd edition, 1993).

A newly synthesized biopolymer may be further chemically modified, e.g., glycosylated, acetylated, PEGylated, etc. before use. Subject biopolymers can be purified, for example, by high performance liquid chromatography (HPLC), and can be characterized using, for example, mass spectrometry or sequence analysis, prior to use in the subject methods.

A polymer of interest may be at least 2, 3, 4, 5, 6, 7, 8, 9, 10, 11 or 12 monomers, or more than 12 monomers in length, usually up to about 20, 30, 40, 50 or 100 or 1000 or more monomers in length. Accordingly, a peptide employed in the subject methods may contain at least 2, 3, 4, 5, 6, 7, 8, 9, 10, 11 or 12 amino acids, or more than 12 amino acids, usually up to about 20, 30, 40 or 50 amino acids (e.g., non-naturally occurring amino acids, naturally occurring amino acids or a mixture thereof). Polymers of particular interest are 2-50, 3-40, 4-30, 3-8,5-20 or 6-10 monomers in length, and typically range from 500-5000 Da, 600-4000 Da, 700-2000 Da in molecular weight. The subject polymers may be described using the formula $X_{(n)}$, where X is any monomer, and n is the number of those monomers in the polymer, e.g., as exemplified above. $X_1$ is the first monomer in a subject polymer, and $X_n$ is the last monomer in the polymer.

Figure 2:
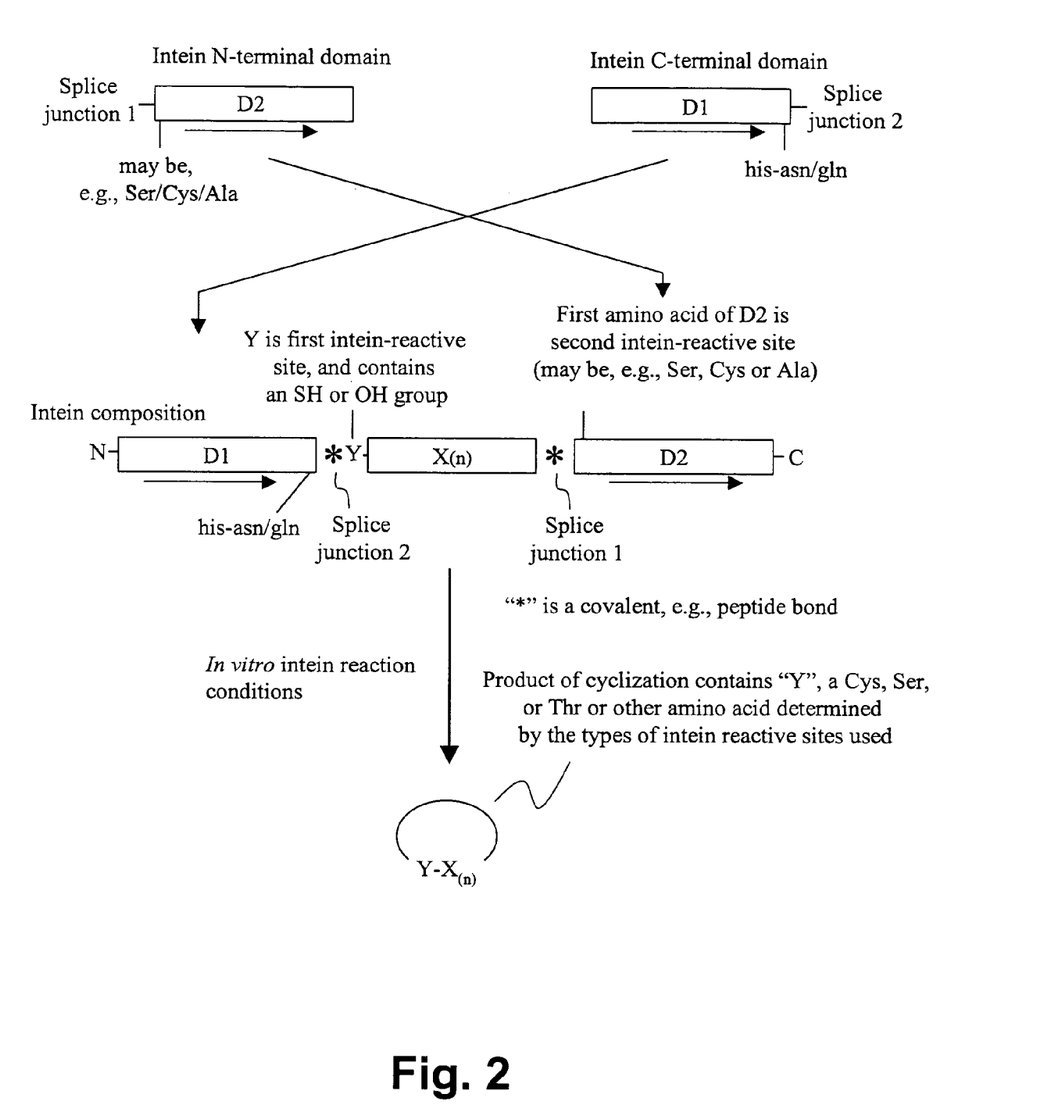
FIG. 2 is a second schematic representation of an embodiment of the invention.

The monomer at one end of the subject polymer, typically the N-terminal end of the polymer is a polypeptide, is usually an intein-reactive amino acid, i.e., an amino acid that can be joined to another amino acid by an intein. The intein-reactive amino acid of the polymer contains a hydroxyl (OH) or thiol (SH) group (e.g., a cys, ser or thr amino acid or analog thereof, etc.). An exemplary subject polymer having sequence $X_{(n)}$ is shown in FIG. 2. Solely for ease of description, the intein reactive site present in the polymer is termed the first intein-reactive site and the intein reactive site present in the second intein domain is termed the second intein-reactive site.

In particular embodiments, and depending on the exact ligation methods used, the monomer at the other end of the polymer (i.e., the C-terminal end if the polymer is a polypeptide) may also be an amino acid. In other embodiments, the monomer at the other end of the polymer (i.e., the C-terminal end if the polymer is a polypeptide) may contain an activatable or activated reactive group (e.g. a group that is activated when the polymer is cleaved from a solid support, for example a resin-activated thioester group), that facilitates ligation of that end of the polypeptide to the second intein domain.

In certain embodiments, a polymer may be a polypeptide containing non-natural amino acids which generally contain any combination of non-natural components, including: a) residue linkages other than natural amide bonds ("peptide bonds"); and/or b) non-natural amino acid residues in place of natural amino acid residues.

Linkages other than natural amide bonds (i.e., —C(=O)NH—) that may be employed in the subject compositions include, but are not limited to: ketomethylene bonds (for example, —C(=O)—CH$_2$—), aminomethylene bonds (CH$_2$—NH), ethylene bonds (—C$_2$H$_4$—), olefin bonds (—CH=CH—), ether bonds (—CH$_2$—O—), thioether bonds (—CH$_2$—S—), tetrazole bonds (CN$_4$—), as well as thiazole, retroamide, thioamide, and ester bonds. Such "surrogate" peptide bonds are well known in the art (see, for example, Spatola (1983) in Chemistry and Biochemistry of Amino Acids, Peptides and Proteins, Vol. 7, pp 267-357, A Peptide Backbone Modifications, Marcell Dekker, NY) and are readily employed herein. For ease of description, such linkages may still termed "peptide" or "amino" bonds herein, although the linkage may not have a conventional "peptide" or "amino" bonds structure: —C(=O)NH—

Further, as mentioned above, a polymer may contain natural or non-natural amino acids, where natural and non-natural amino acids are classified according to Table 1.

The non-natural amino acids of Table 1 are abbreviated as follows: amino β-alanine (β-Ala) and other omega-amino acids such as 3-aminopropionic acid (Dap), 2,3-diaminopropionic acid (Dpr), 4-aminobutyric acid and so forth; α-aminoisobutyric acid (Aib); ε-aminohexanoic acid (Aha); δ-aminovaleric acid (Ava); N-methylglycine or sarcosine (MeGly); ornithine (Om); citrulline (Cit); t-butylalanine (t-BuA); t-butylglycine (t-BuG); N-methylisoleucine (MeIle); phenylglycine (Phg); cyclohexylalanine (Cha);

norleucine (Nle); 2-naphthylalanine (2-Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); α-2-thienylalanine (Thi); methionine sulfoxide (MSO); homoarginine (hArg); N-acetyl lysine (AcLys); 2,3-diaminobutyric acid (Dab); 2,4-diaminobutyric acid (Dbu); p-aminophenylalanine (Phe(pNH$_2$)); N-methyl valine (MeVal); homocysteine (hCys) and homoserine (hSer).

TABLE 1

| Classification | Natural | Non-natural |
|---|---|---|
| Aromatic | F, Y, W | Phg, Nal, Thi, Tic, Phe(4-Cl), |
| Apolar | L, V, I, A, M | Phe(2-F), Phe(3-F), Phe(4-F), Pyridyl Ala, Benzothienyl Ala T-BuA, T-BuG, MeIRe, Nle, MeVal, G, P Cha, MeGly, Aib |
| Aliphatic | A, V, L, I | t-BuA, t-BuG, MeIle, Nle, MeVal, Cha, bAla, MeGly, Aib, Dpr, Aha |
| Acidic | D, E | phenyl alanine para-carboxylic acid |
| Basic | H, K, R | Dpr, Orn, hArg, Phe(p-NH$_2$), Dbu, Dab |
| Polar | Q, N, S, T, Y | Cit, AcLys, MSO, hSer, bAla |
| Cysteine-Like | C | Pen, hCys, p-methyl Cys |

Each class of amino acids set forth in Table 1 is discussed in greater detail below:

A hydrophobic amino acid is an amino acid exhibiting a hydrophobicity of greater than zero according to the normalized consensus hydrophobicity scale of Eisenberg et al. (1984, J. Mol. Biol. 179: 125-142). Examples of natural hydrophobic amino acids include Pro, Phe, Trp, Met, Ala, Gly, Tyr, Ile, Leu and Val. Examples of non-natural hydrophobic amino acids include t-BuA.

An aromatic amino acid is a hydrophobic amino acid having a side chain containing at least one aromatic or heteroaromatic ring. The aromatic or heteroaromatic ring may contain one or more substituents such as —OH, —SH, —CN, —F, —Cl, —Br, —I, —NO$_2$, —NO, —NH$_2$, —NHR, —NRR, —C(O)R, —C(O)OH, —C(O)OR, —C(O)NH$_2$, —C(O)NHR, —C(O)NRR and the like where each R is independently optionally substituted C$_1$-C$_6$ alkyl, optionally substituted C$_1$-C$_6$ alkenyl, optionally substituted C$_1$-C$_6$ alkynyl, optionally substituted C$_6$-C$_{20}$ aryl C$_0$-C$_6$ alkyl and optionally substituted C$_5$-C$_{15}$ heteroaryl C$_0$-C$_6$ alkyl. Examples of natural aromatic amino acids include Phe, Tyr and Trp. Commonly encountered non-natural encoded aromatic amino acids include phenylglycine, 2-naphthylalanine, β-2-thienylalanine, 1,2,3,4-tetrahydroisoquinolin-e-3-carboxylic acid, 4-chloro-phenylalanine, 2-fluorophenylalanine, 3-fluorophenylalanine and 4-fluorophenylalanine. Aromatic rings of a non-natural amino acid include, thiazolyl, thiophenyl, pyrazolyl, benzimidazolyl, naphthyl, furanyl, pyrrolyl, and pyridyl aromatic rings.

An "apolar" or "non-polar" amino acid is a hydrophobic amino acid having a side chain that is uncharged at physiological pH and which has bonds in which the pair of electrons shared in common by two atoms is generally held equally by each of the two atoms (i.e., the side chain is not polar). Examples of natural apolar amino acids include Gly, Leu, Val, Ile, Ala and Met. Examples of non-natural apolar amino acids include Cha.

An aliphatic amino acid is a hydrophobic amino acid having an aliphatic hydrocarbon side chain. Examples of natural aliphatic amino acids include Ala, Leu, Val and Ile. Examples of non-natural aliphatic amino acids include Nle.

A hydrophilic amino acid is an amino acid exhibiting a hydrophilicity of less than zero according to the normalized consensus hydrophobicity scale of Eisenberg et al. (1984, J. Mol. Biol. 179: 125-142). Examples of natural hydrophilic amino acids include Thr, His, Glu, Asn, Gln, Asp, Arg, Ser and Lys. Examples of natural hydrophilic amino acids include Cet and hCys.

An acidic amino acid is a hydrophilic amino acid having a side chain pK value of less than 7. Acidic amino acids typically have negatively charged side chains at physiological pH due to loss of a hydrogen ion. Examples of natural acidic amino acids include Asp and Glu.

A basic amino acid is a hydrophilic amino acid having a side chain pK value of greater than 7. Basic amino acids typically have positively charged side chains at physiological pH due to association with hydronium ion. Examples of natural basic amino acids include Arg, Lys and His. Examples of non-natural basic amino acids include the non-cyclic amino acids ornithine, 2,3-diaminopropionic acid, 2,4-diaminobutyric acid and homoarginine.

A polar amino acid is a hydrophilic amino acid having a side chain that is uncharged at physiological pH, but which has one bond in which the pair of electrons shared in common by two atoms is held more closely by one of the atoms. Examples of natural polar amino acids include Ser, Thr, Asn and Gln. Examples of non-natural polar amino acids include citrulline, N-acetyl lysine and methionine sulfoxide.

The amino acid residue Cys has the ability to form disulfide bridges with other Cys residues or other sulfanyl-containing amino acids. Cys is classified as a polar hydrophilic amino acid for the purposes of the present invention. Typically, cysteine-like amino acids generally have a side chain containing at least one thiol (SH) group. Examples of genetically encoded cysteine-like amino acids include Cys. Examples of non-genetically encoded cysteine-like amino acids include homocysteine and penicillamine.

Further non-natural amino acids are described in U.S. patent application Ser. No. 10/197,927, published as US20030166138, which publication is incorporated herein for all purposes.

Exemplary 3-monomer and 4-monomer-containing cyclic polymers that may be made using the methods described herein may be found U.S. provisional patent applications each entitled "INHIBITORS OF IRES-MEDIATED TRANSLATION AND METHODS OF USE" (60/677,159, 60/677,041, 60/677,200 and 60/677,030), filed on May 2, 2005.

Ligation Methods

As discussed above, a first intein domain, a second intein domain, and a subject polymer are ligated together to form an intein composition having the formula $D1-X_{(n)}-D2$, where "—" is a covalent bond, typically a peptide bond. A wide variety of methods are available for ligating polypeptides to polymers via peptide bonds, particularly polymers that contain amino acids both of their ends. Accordingly, a subject intein composition may be made a number of ways.

Typically, the subject intein compositions are made using a "step-wise" approach, however, because different methods may ligate only certain amino acids and not others, and because amino acids may be specifically chosen because they can be ligated to each other and not to others (e.g., through a chemoselective reaction), certain embodiments of the subject ligation methods do not require that the components are ligated using a stepwise approach, e.g., the components are simultaneously ligated in a single reaction vessel. If a stepwise approach is used, the first or the second intein domain is first ligated to the polymer to form an intermediate product, and the remaining intein domain is ligated to the intermediate product to form a subject intein composition. If such stepwise methods are used, one end of the polymer may be protected, as discussed above, until the intermediate product has formed. Upon production of the intermediate product, the polymer may be de-protected, allowing that end of the polymer to react with the remaining intein domain to form a subject intein composition.

Methods for ligating polypeptides to amino acid-containing synthetic polymers via peptide bonds are well known in the art and are described in Dawson and Kent (*Synthesis of Native Proteins by Chemical Ligation*, Annu. Rev. Biochem. 2000, 69:923-60). In particular embodiments, the polypeptide and polymer are linked using a process called "native chemical ligation" in which an N-terminal sulfhydryl- (i.e., thiol-) containing peptide is chemically ligated to a peptide having a C-terminal thioester group, with the resultant formation of a peptide bond at the ligation site (see e.g., U.S. Pat. No. 6,184,344 and Dawson et al. (Science. 1994 266:776-9)). Such methods may be used to ligate any amino acid at the C-terminus of a peptide to an N-terminal sulfhydryl group of a second peptide (e.g., a cysteine residue of the second peptide, or any other sulfhydryl-containing amino acid). See Hackeng et al. (Proc. Natl. Acad. Sci. 1999 96: 10068-10073) for a description of these native chemical ligation methods. In addition to sulfhydryl-containing amino acids, native chemical ligation methods have also be used to ligate peptides that have a C- or N-terminal naturally occurring glycine, and other amino acid (see U.S. Pat. No. 6,307,018). Further methods for ligating an intein to a polymer are described in Muir et al. (Proc. Natl. Acad. Sci. 1998 95:6705-6710) and published U.S. published patent application 20020151006. Muir et al and 20020151006 generally provide methods in which a precursor polypeptide is cleaved using a thiol cofactor, e.g., thiophenol, MESNA, or the like, to produce a polypeptide with a reactive thioester group that can be ligated to any peptide having an N-terminal unprotected sulphydryl group. Finally, Evans et al. (U.S. published patent application 20030013148) discuss an intein-related method in which polypeptides can be ligated together on a solid support.

Other ligation methods suitable for use in the subject methods are described in Schlolzer et al. (Science 1992 256:221-225), Rose et al. (Am. Chem. Soc. 1994 116:30-34); Liu et al. (Proc. Natl. Acad. Sci, 1994 91:6584-6588), Canne et al. (J.

Am. Chem. Soc. 1995 117:2998-3007) and Baca et al. (J. Am. Chem. Soc. 1995 117: 1881-1887).

According, the instant methods generally involve ligating first and second recombinant intein domains to a synthetic polymer to form a compound containing the structure $D_1$-$X_{(n)}$-$D_2$, where $D_1$ is a first catalytic domain of an intein; $X_{(n)}$ is a polymer containing n residues of a monomer X, where n is at least 2, and wherein the polymer has a first reactive site for the intein at one end (typically its N-terminus if the polymer is a peptide); and where $D_2$ is a second catalytic domain of an intein, said second catalytic domain having at its N-terminus a second reactive site for the intein.

In many embodiments, the ligation methods involve ligating a first catalytic domain of an intein with a synthetic polymer to produce a compound of the formula $D_1$-$X_{(n)}$, where $D_1$ and $X_{(n)}$ are joined by a first peptide bond, and ligating said second catalytic domain of an intein with said synthetic polymer to produce a compound of the formula $D_1$-$X_{(n)}$-$D_2$ where $D_1$ and $X_{(n)}$ are joined by a second peptide bond.

In certain embodiments, the subject ligation methods involve ligating a first catalytic domain of an intein having a C-terminal reactive thioester with a synthetic polymer, said synthetic polymer having a sulfhydryl group at one terminus and a protected thioester group at the other terminus to produce a compound of the formula: $D_1$-$X_{(n)}$-Z, where $D_1$ is said first catalytic domain of an intein, $X_{(n)}$ is a polymer containing n residues of a monomer X, where n is at least 2, and Z is a protected thioester group, deprotecting the protected terminal thioester group to produce a terminal reactive thioester group; and ligating the terminal reactive thioester group with said second catalytic domain of an intein having an N-terminal sulfhydryl group to produce a compound of the formula: $D_1$-$X_{(n)}$-$D_2$.

As discussed above, the first and second reactive sites may contain sulfhydryl or hydroxyl groups (e.g., cys, ser, thr), or, in certain embodiments, may be an ala or analog thereof.

Accordingly, a first intein domain, a second intein domain, and a subject polymer are ligated together to form an intein composition having the formula D1*$X_{(n)}$*D2, where "*" is a peptide bond. The above discussion describes a method in which the first intein-reactive site is donated to the intein composition via the first monomer of the polymer and the second reactive site is donated to the intein composition via the first amino acid of the second intein domain. It is recognized that the same intein composition can be made by donating the first intein-reactive site via the C-terminus of the first intein domain and/or by donating the second intein-reactive site via the N-terminus of the polymer. Accordingly, when an intein composition having the structure $D_1$-$X_{(n)}$-$D_2$, $D_2$ having a first reactive site at its N-terminus (i.e., the end closest to the N-terminus of the intein composition) a first intein reactive site and $X_{(n)}$ having a second reactive site for said intein at its N-terminus, or grammatical equivalents thereof, is recited, intein compositions made by these other methods are encompassed.

Intein Reaction Conditions

Once made, an intein composition is typically maintained in intein reaction conditions to produce a cyclic peptide via an autocatalytic process (see FIG. 2). Intein reaction conditions may vary depending on the intein used and if such conditions are not already known, they can be readily determined without undue effort. In vitro intein reaction conditions for many inteins are known (Yamazaki, et al., J. Am. Chem. Soc. 120: 5591-5592 (1998), Wu, et al., Biochim. Biophys Acta, 1387: 422-432 (1998), Mills, et al., Proc. Natl. Acad. Sci. USA, 95(7):3543-3548 (1998), Otomo, et al., J. Biomol. NMR, 14(2):105-114, Otomo, et al. Biochemistry, 39(49):16040-16044. and Southworth, et al., EMBO J., 17(4):918-926 (1998)), and may be readily used in the instant methods. In particular embodiments, salt concentration, pH, or temperature of the intein composition may be adjusted to provide intein reaction conditions. In other embodiments, a molecule, e.g., a reducing agent or denaturant, may added to provide intein reaction conditions.

For example, the Ssp DnaE split intein is less active at 37° C. than at 15° C., and is less active at pH>10 than at a neutral pH. Similarly, the Ssp DnaB intein used in the example set forth below is active at 25° C. at pH 7.0, and inactive at 4° C. Prior to the cyclization reaction, the intein composition is typically maintained in conditions that are not intein reaction conditions, e.g., 4° C.

If desired, cyclic polymers produced by the above methods may be separated from the intein bioproducts using any suitable means, including size exclusion chromatography, filtration or by affinity chromatography, e.g., employing affinity tags that are part of the intein domains used.

Compositions Produced by the Subject Methods

Intein Compositions

The invention provides an intein composition having the structure: $D_1$-$X_{(n)}$-$D_2$, where $D_1$ is a first catalytic domain of an intein; $D_2$ is a second catalytic domain of an intein having at its N-terminus a first reactive site for said intein, and where $X_{(n)}$ is a polymer having n residues of a monomer X, wherein n is at least 2, and where the polymer has a second reactive site for said intein at its N-terminus. In certain embodiments, the first and second ends of a polymer that is part of an intein composition are designated as the "N-terminus" and "C-terminus" of the polymer. These designations are solely intended to indicate the orientation of the polymer in an intein composition and are not meant to imply that the polymer is a polypeptide, or that it contains any amino acids. In other words, the end of a polymer that is joined to the C-terminal end of $D_1$ is designated as the N-terminus of the polymer, and the end of the polymer that is joined to the N-terminal end of $D_2$ is designated as the C-terminus of the polymer. Accordingly, while a polymer may contain no amino acids and may not be a polypeptide, it may still contain an N-terminal end and a C-terminal end. As shown in FIG. 2, intein compositions contain an N-terminus and a C-terminus by virtue of the fact that the intein compositions contain proteinaceous intein domains. The N-terminus of the polymer portion of an intein composition is the end of the polymer that is closest to the N-terminus of intein composition. Similarly, the C-terminus of a polymer portion of an intein composition is the end of the polymer that is closest to the C-terminus of the intein composition. As discussed above, $D_1$, $X_{(n)}$ and $D_2$ are typically joined by covalent, e.g., peptide, bonds. In certain embodiments, therefore, the intein compositions described herein are of the formula D1*$X_{(n)}$*D2, where "*" is a peptide bond.

An intein composition produced by the subject methods is a catalytically active intein that is capable of autocatalytically cyclizing the polymer which is part the intein composition under intein reaction conditions. Such intein compositions therefore typically have two intein reactive sites, one positioned at the N-terminus of the polymer and the other positioned at the N-terminus of the C-terminal intein domain (see FIG. 2). As discussed above, intein reactive sites typically, although not always, are amino acids containing an OH or SH group (e.g., cys, ser or analogs thereof) or an ala or analog thereof and in certain embodiments, the C-terminal amino acid of the N-terminal intein domain may contain an his-asn/ gln motif, although other motifs are readily used. FIG. 2 shows an intein composition having many of the features described above.

Since a subject intein composition may contain a synthetic biopolymer, e.g., containing analogs of naturally occurring monomers, e.g., amino acids, it may be referred to as a "semi-synthetic" composition in which a first part of the composition (i.e., the C- and N-terminal intein domains) are made in a cell, and a second part of the composition (i.e., the polymer) is made synthetically. As discussed above, the polymer region of an intein composition may contain one or many non-naturally occurring amino acids and in certain embodiments, may contain only non-naturally occurring amino acids.

In certain embodiments, a subject intein composition may be part of a library of intein compositions containing polymers of different chemical structure. Such libraries are typically used to produce libraries of cyclic polymers for use in drug screening assays. For example, subject polymers, e.g., polypeptides, may contain a randomized sequence of monomers, e.g., nucleotides and/or amino acids. Since a wide variety of chemistries are available for the synthetic production of polymers, intein compositions containing an almost limitless number of different polymers could be made. Typically, the subject intein composition libraries contain a plurality (i.e., at least 5, 10, 20, 50, 100, 200, 500, 1000, 2000, 5000, 10,000, 50,000, 100,000, usually up to about 500,000 or 1,000,000 or more) of different intein compositions (i.e., intein compositions containing polymer regions of different chemical structure, e.g., different sequences of monomers).

In certain embodiments, a subject intein composition library contains a mixture of different intein compositions. In other embodiments, however, a subject intein composition library does not contain a mixture of intein compositions. In such embodiments, each member of an subject library may be separately aliquoted in a suitable container, e.g., a tube or well of a multi-well plate.

As will be discussed in greater detail below, the product cyclic peptides contain an amino acid "Y" that is produced by the reaction between the two intein reactive sites of the intein composition. Accordingly, in some embodiments, the subject intein composition may be described by the formula $D_1$-Y—$X_n$-$D_2$ or $D_1$-$X_n$—Y-$D_2$, where Y is an amino acid containing a OH or SH group, e.g., a cys, ser or thr, or analog thereof.

Cyclic polymers produced using the above-described methods may contain a biopolymer of interest, as described above, plus at least one amino acid that is produced as a product of an intein-mediated reaction between the first and second reactive sites in an intein composition. This amino acid may be ser, cys or thr. However, since a wide range of chemistries are available, other amino acids, including naturally occurring and non-naturally occurring amino acids containing an SH or OH group, for example, may be present. An exemplary cyclic polymer is shown at the bottom of FIG. 2, wherein "Y" is an intein reaction product amino acid as discussed above. Accordingly, all positions of a subject cyclic polymer except for one position—that of "Y"—may be variable, and are determined by the sequence of the polymer used. One position of a subject cyclic polymer is typically non-variable, and is determined by the chemistry of the intein reactive sites used.

Accordingly, cyclic peptides produced by the subject methods typically comprise the structure:

where Y is an amino acid incorporated as a result of the intein-mediated reaction between the first and second reactive sites in an intein composition, and $X_{(n)}$ is a polymer, as discussed above. Y can be ser, cys or thr or another amino acid, for example.

In particular embodiments, a cyclic polymer produced by the instant methods may contain 2, 3, 4, 5, 6, 7, 8, 9, or 10 or more monomers, and may further include the "Y" amino acid discussed in the previous paragraph.

In certain embodiments, a subject cyclic polymer may be part of a library of cyclic polymers, each member of the library having a different chemical structure. For example, the subject cyclic polymers, may contain a randomized sequence of monomers, e.g., nucleotides and/or amino acids. Since a wide variety of chemistries are available for the synthetic production of polymers, the subject cyclic polymers libraries may contain an almost infinite number of chemical structures. Typically, a subject cyclic polymer libraries contains a plurality (i.e., at least 5, 10, 20, 50, 100, 200, 500, 1.000, 2000, 5000, 10,000, 50,000, 100,000, usually up to about 500,000 or 1,000,000 or more) of different cyclic polymers (e.g., cyclic biopolymers having different chemical structures, for example, different sequences of monomers).

In certain embodiments, a subject cyclic peptide library contains a mixture of different cyclic peptides. In other embodiments, however, a subject cyclic polymer library does not contain a mixture of cyclic polymers. In such embodiments, each member of an subject library may be separately aliquoted in a suitable container, e.g., a tube or well of a multi-well plate.

Utility

The subject methods and compositions may be used to make a cyclic polymer. The subject methods and compositions find particular use in producing cyclic polymers, particularly biopolymers that are not genetically encodable. The subject methods may also be used for producing libraries of cyclic polymers, particularly libraries of cyclic peptides, for use in screening assays to identify biologically active cyclic polymers. In certain embodiments, such a biologically active cyclic polymer may be used as a drug to treat a disease or condition, e.g., cancer, an inflammatory disease or an infection.

In typical embodiments, a library of cyclic polymers is made using the methods set forth above, and the cyclic polymers of the library are each assayed for biological activity. Such assays are well known in the art and include cell-free assays and cellular assays.

In particular embodiments, the subject methods find use in screening for variants of a known biologically active cyclic peptide that have an improved activity. In these embodiments, variants of a cyclic peptide known to have a biological activity, e.g., a peptide having anti-microbial (e.g., cyclic peptide inhibitors of beta(1,3)glucan synthesis (Tkacz et al. Curr Opin Microbiol. 2001 4:540-5) or cyclic peptide antibiotics (e.g. Kohli et al. Nature. 2002 418:658-61; Tsubery et al., Peptides. 2001 October; 22(10):1675-81), anti-cancer activity, (e.g., triostin A, Yang et al., Prep Biochem Biotechnol. 2002 32:381-91) or any other activity, e.g., anti-sepsis activity (Vallespi et al., Int Immunopharmacol. 2003 3:247-56), are synthesized by a machine, cyclized using the above-described methods, and assayed to determine if the variant has an improved activity.

The subject methods find particular use in production of cyclic polymers. In particular, the subject methods find particular use in producing cyclic polymers (e.g., cyclic peptides) that are not genetically encodable, using a cell-free system. For example, the subject methods may be used to produce cyclic peptides having non-naturally occurring or non-encodable amino acids, or cyclic peptides that cannot be produced in a cell by any means. Since the subject methods are straightforward, highly efficient, scalable and result in a product that is already highly purified and not modified or contaminated with cellular materials, the methods find particular use in manufacture of cyclic polymers for clinical investigations, and for therapeutic uses. Cyclic polymers identified using any method may be produced using the methods described herein.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the subject invention.

Example 1

The method outlined in example 1 relies on a series of chemical ligation steps in which the two functional domains of an intein are successively ligated to the flanking ends of a synthetically produced polymer. The resulting intein, reconstituted so that it now contains a synthetic polymer positioned within it's active site, is then capable of enzymatically cyclizing the polymer. The chemical ligation steps involved in the joining together of the two intein domains and the synthetic polymer utilize the selective reaction of C-terminal thioesters with sulfhydrl-containing amino acids positioned on the N-terminus of the reacting partner. This chemical approach is used, step-wise, to first ligate the C-terminal domain of the SsB DnaB intein to one end of a synthetic polymer and then used again to ligate the N-terminal domain of SsB DnaB to the remaining end. Each ligation step involves the generation of two starting intermediates; one partner contains a C-terminal thioester and the other reacting partner contains a N-terminal sulfhydrl-containing residue/amino acid. The individual steps outlined in example 1 describe how each starting intermediate is first generated and then how these intermediates are reacted, in series, to obtain the final product. FIG. 3 shows a five step reaction that may be used to cyclize a peptide containing three monomers of X.

Figure 3A:
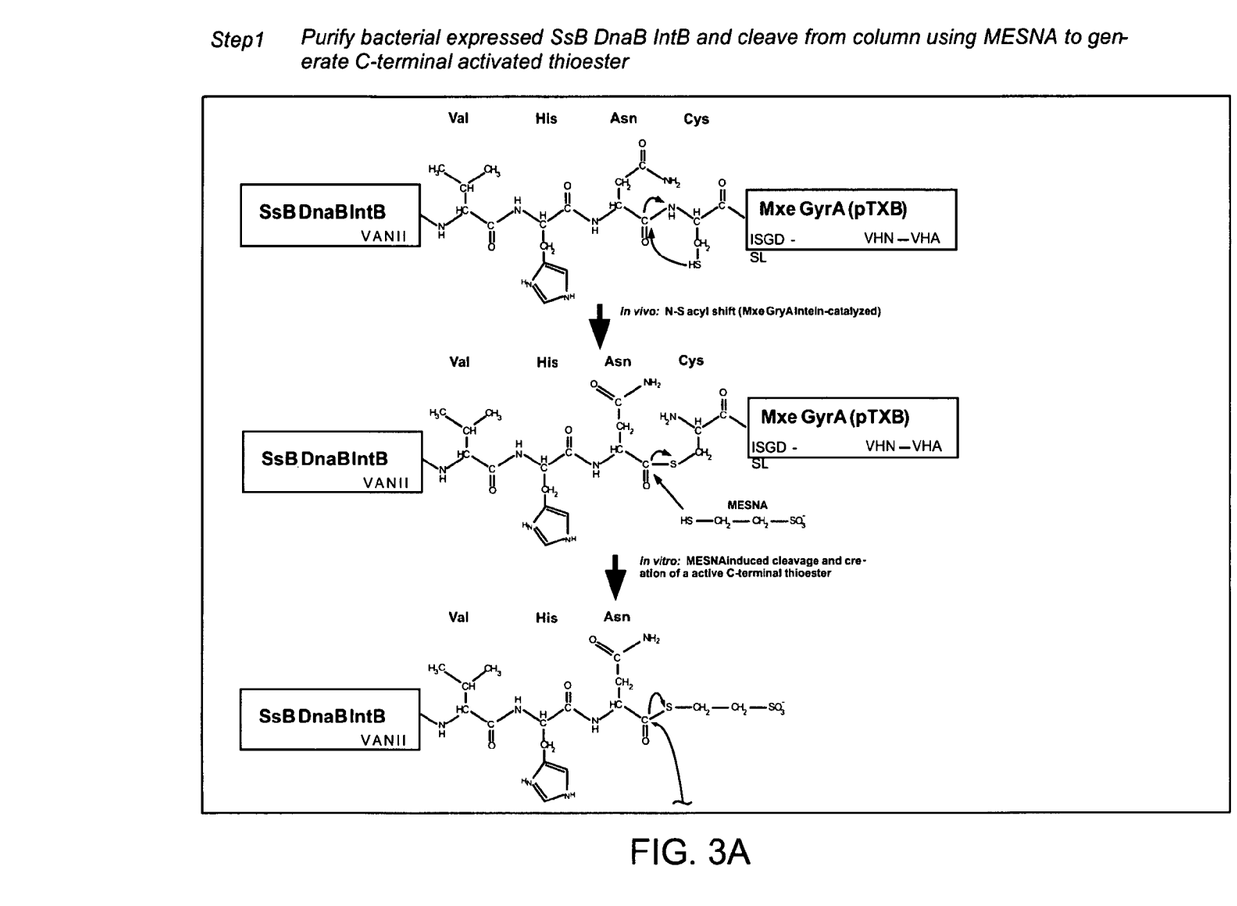
FIGS. 3A-3E show an exemplary method for producing a synthetic cyclic polymer using an intein.

FIG. 3A (Step 1) describes a method whereby the C-terminal domain of the SsB DnaB intein is produced in such a way that it contains a C-terminal thioester. Since proteins typically do not naturally terminate with this chemical entity, a combination of enzymatic and chemical modifications can be used to generate the desired C-terminal thioester. In the example described here, a second, mutated intein (derived from the Mxe GyrA intein; colored green) is first placed downstream of the C-terminus of the SsB DnaB intein domain. The downstream Mxe GyrA intein catalyzes the formation of a stable thioester linkage at the junction site between itself and the upstream SsB DnaB intein domain. This thioester link is then selectively cleaved by addition of the reducing agent MESNA, thereby liberating the SsB DnaB intein domain with a C-terminal thioester. This is the first of three components that are necessary for the generating the final reconstituted intein capable of cyclizing a synthetic polymer.

Figure 3B:
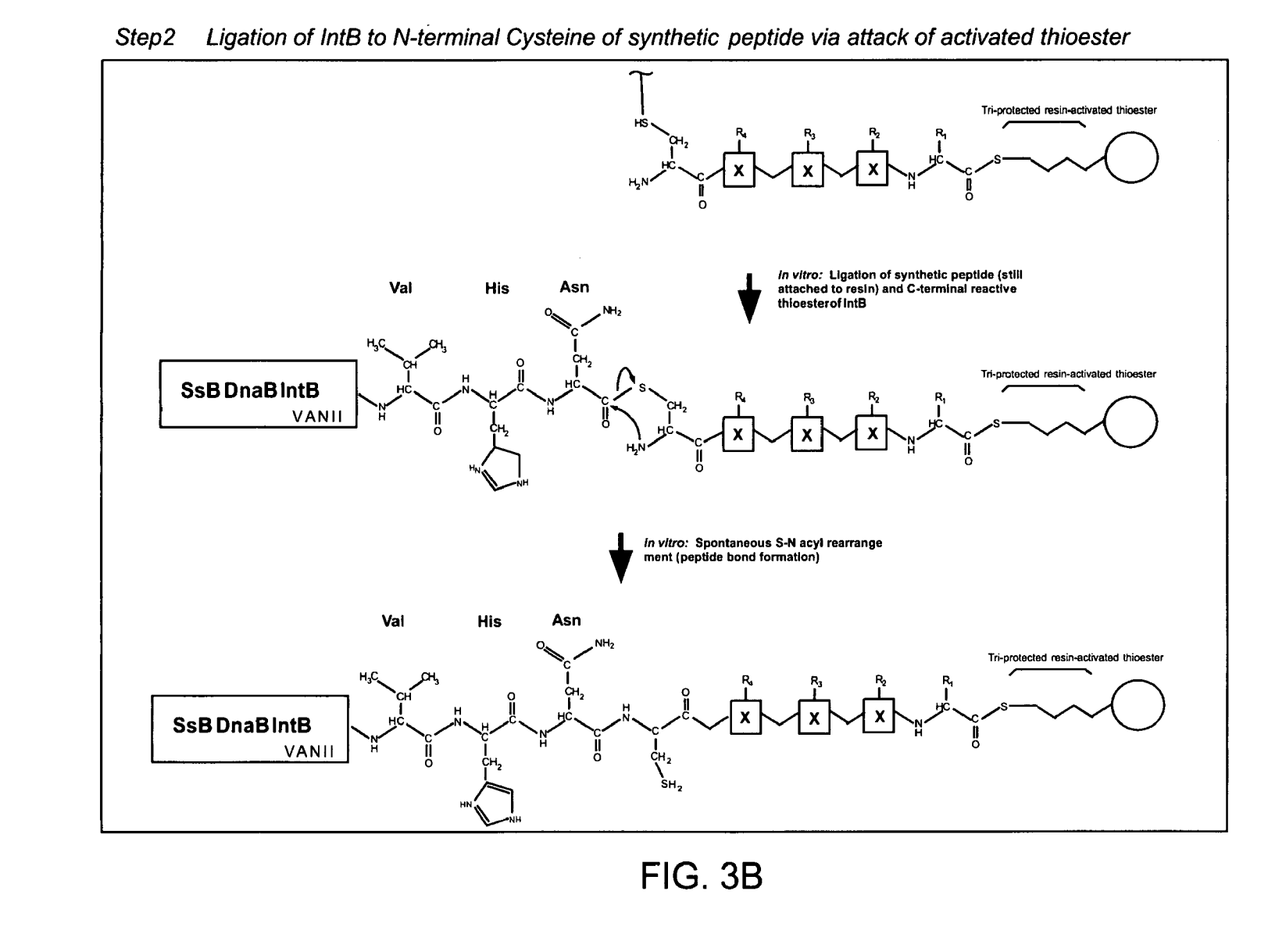

FIG. 3B (Step 2) describes certain features of the second component, the synthetic polymer, and the method by which it is ligated to the first component, the SsB DnaB intein C-terminal domain. The synthetic polymer is produced such that it possesses a sulfhydryl-containing amino acid (e.g. cysteine) at its N-terminus and a tri-protected resin-activated thioester linkage attached to a solid phase support at it's C-terminus. Chemical ligation of the synthetic polymer to the SsB DnaB C-terminal domain occurs via nucleophilic attack by the synthetic polymer's N-terminal sulfhydrl group on the carbonyl group of the SsB DnaB's C-terminal thioester. The resulting ligation intermediate subsequently undergoes a spontaneous S—N acyl rearrangement, converting the junction between the SsB DnaB intein C-terminus and the synthetic polymer into a peptide bond. The resulting product is referred to as the two-component intermediate.

Figure 3C:
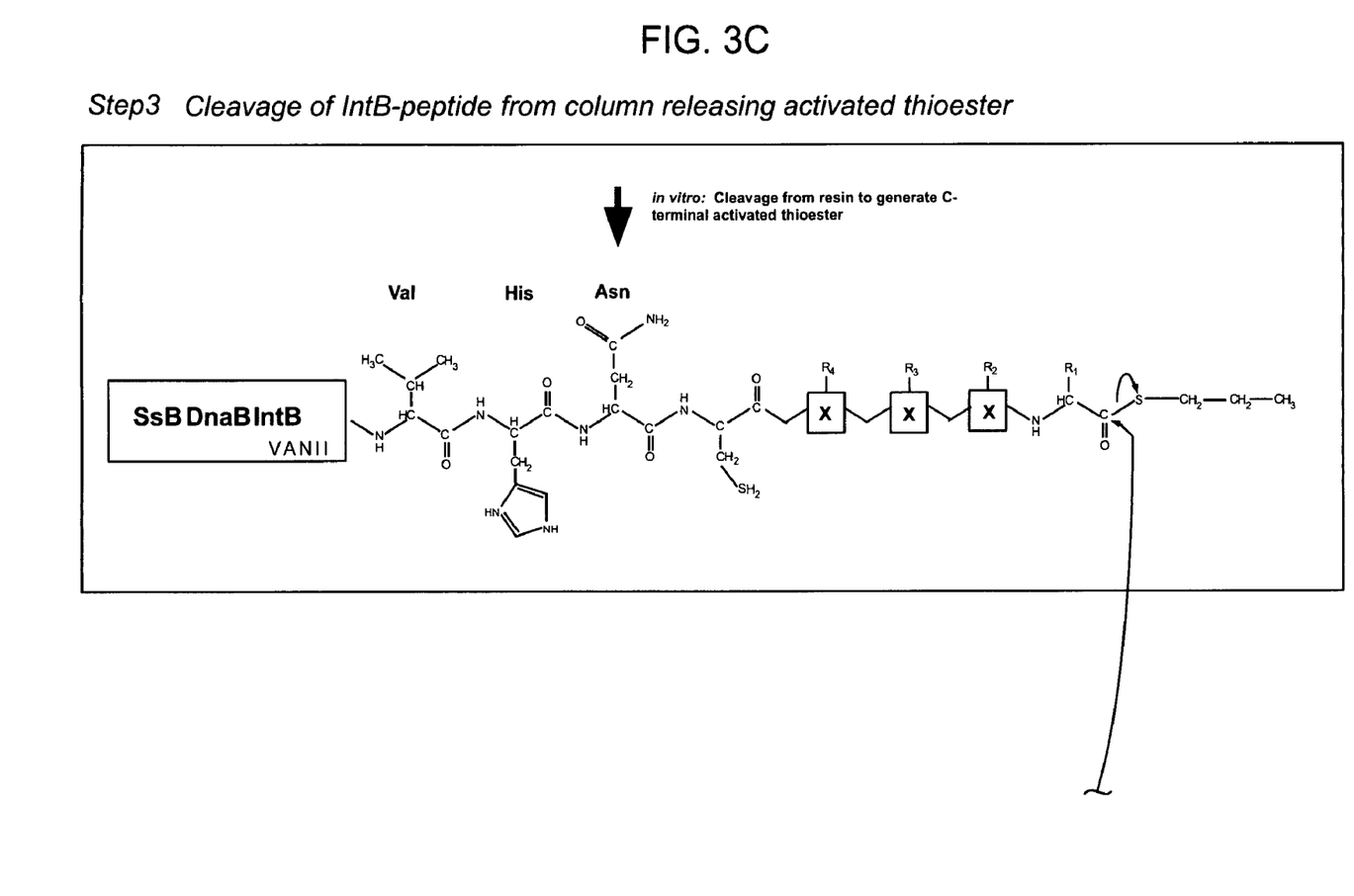

FIG. 3C (Step 3). This two-component intermediate is prepared for the final ligation step by releasing the protecting moieties from the resin and thereby making it's thioester linkage chemically accessible. This deprotection step, sometimes referred to as "activation", is usually triggered by addition of an acid or base, depending on the specific resin chemistry present. Once activated, the thioester linkage can be cleaved by reaction with the reducing agent MESNA, thereby generating a C-terminal thioester on the two-component intermediate.

Figure 3D:
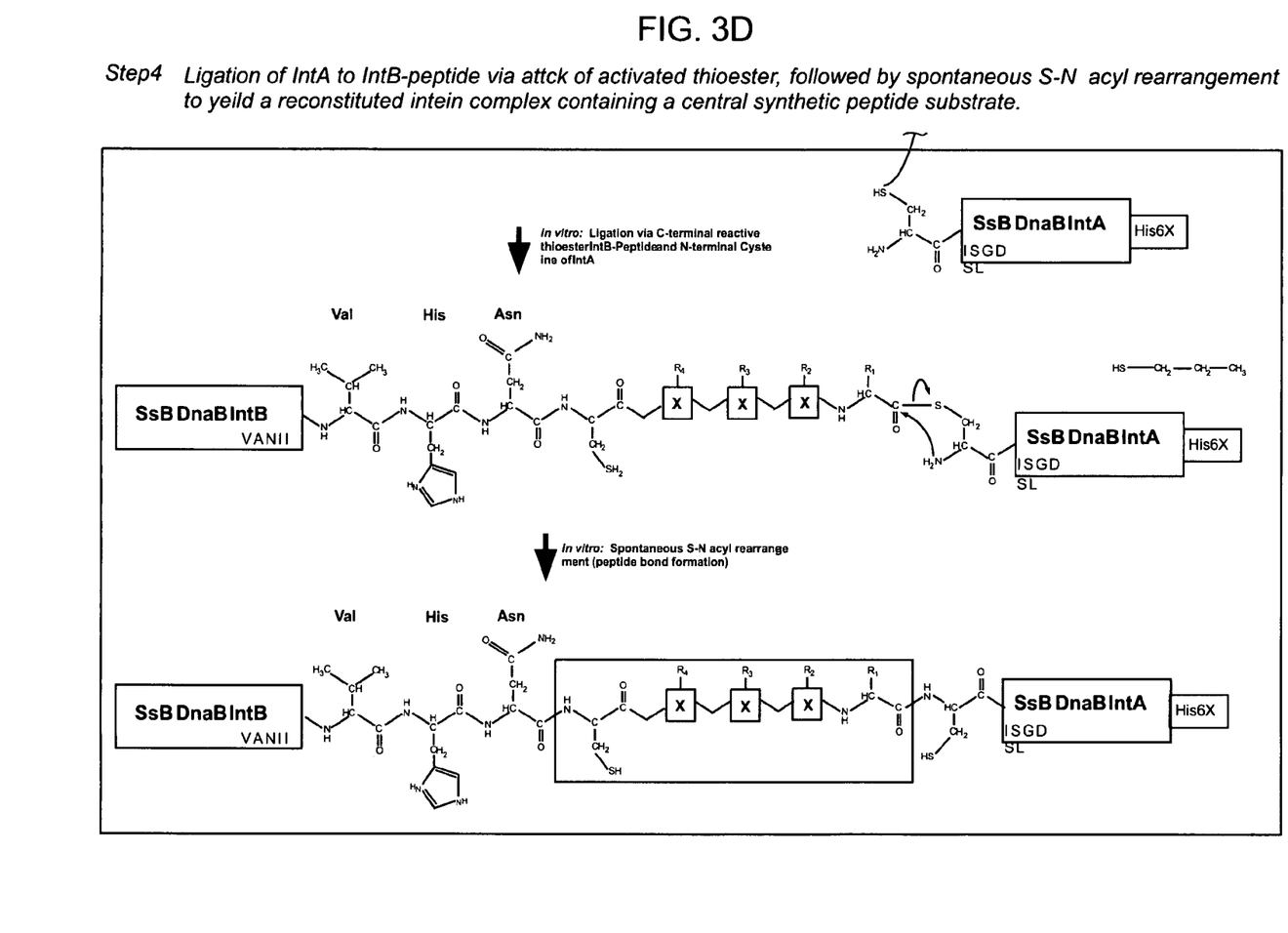

FIG. 3D (Step 4). In a process analogous to that outlined in step one, reaction of the C-terminal thioester of the two-component intermediate with the N-terminal sulfhydrl group of the third component (N-terminal domain of the SsB DnaB intein) leads to a fully reconstituted intein capable of cyclizing the synthetic polymer that has been ligated into it's active site.

Figure 3E:
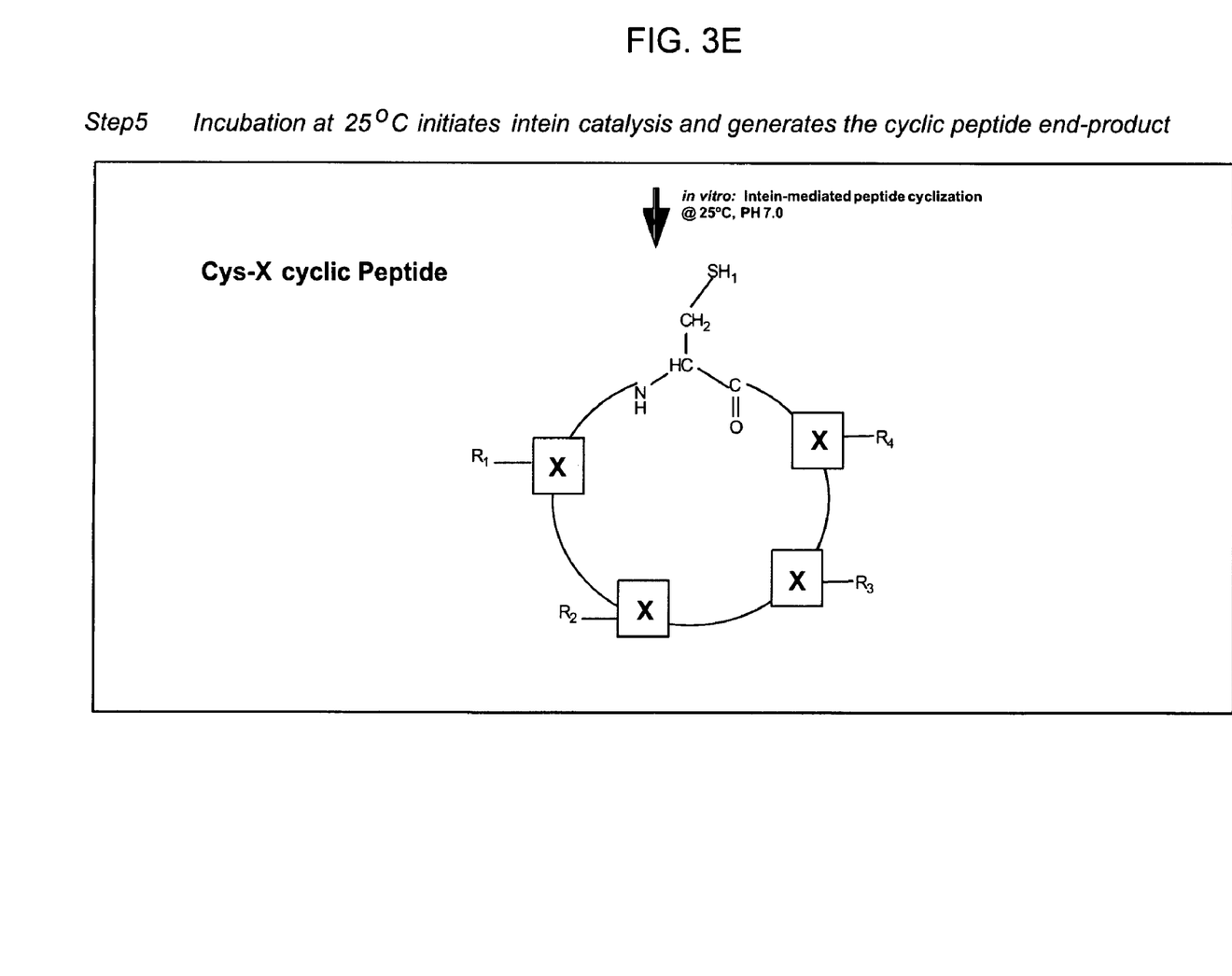

FIG. 3E (Step 5) Altering the reaction conditions appropriately facilitates the intein catalyzed cyclization of the synthetic polymer.

It is evident from the above discussion that the subject invention provides an important new means for producing cyclic polymers, including cyclic peptides having non-naturally occurring amino acids. As such, the subject methods and systems find use in a variety of different applications, including research, medical, therapeutic and other applications, including drug screening. Accordingly, the present invention represents a significant contribution to the art.

What is claimed is:

1. A method comprising:
   native chemical ligating a first isolated intein domain $D_1$ and a second isolated intein domain $D_2$ to polymer $X_{(n)}$ in a cell-free system to produce a compound comprising the structure:

$D_1$-$X_{(n)}$-$D_2$ wherein:

polymer $X_{(n)}$ comprises n residues of a monomer X, wherein n is at least 2, and polymer $X_{(n)}$ is not made up of only naturally-occurring amino acid monomers;

said compound comprises a first intein reactive site at the N-terminus of polymer $X_{(n)}$;

said compound comprises a second intein reactive site at the N-terminus of $D_2$; and said compound produces a cyclic product comprising said polymer, wherein said cyclic product is cyclized via a reaction that joins said first intein reactive site and said second intein reactive site.

2. The method of claim 1, wherein said ligating comprises:

ligating said first intein domain $D_1$ with said polymer $X_{(n)}$ to produce a compound of the formula:

$$D_1\text{-}X_{(n)}$$

wherein $D_1$ and $X_{(n)}$ are joined by a first peptide bond; and, ligating said second isolated intein domain $D_2$ with said polymer $X_{(n)}$ to produce a compound of the formula:

$$D_1\text{-}X_{(n)}\text{-}D_2$$

wherein $D_1$ and $X_{(n)}$ are joined by a second peptide bond.

3. The method of claim 1, wherein said ligating comprises:

ligating a first intein domain $D_1$ having a C-terminal reactive thioester with said polymer $X_{(n)}$, said polymer $X_{(n)}$ having an N-terminal sulfhydryl group and a protected C-terminal thioester group, said ligating producing a compound of the formula:

$$D_1\text{-}X_{(n)}\text{—}Z$$

wherein polymer $X_{(n)}$ comprises n residues of a monomer X, wherein n is at least 2, and Z is said protected C-terminal thioester group, deprotecting said protected C-terminal thioester group to produce a C-terminal reactive thioester group; and ligating said C-terminal reactive thioester group with said second intein domain $D_2$ having an N-terminal sulfhydryl group to produce a compound of the formula:

$$D_1\text{-}X_{(n)}\text{-}D_2$$

4. The method of claim 1, wherein said polymer comprises at least one non-naturally occurring monomer.

5. The method of claim 1, wherein said polymer comprises at least one amino acid monomer.

6. The method of claim 1, wherein said polymer comprises at least one nucleotide monomer.

7. The method of claim 1, wherein said first and second intein reactive sites comprise sulfhydryl or hydroxyl moieties.

8. The method of claim 7, wherein said first and second intein reactive sites comprise cysteine, alanine or serine, or an analog thereof.

9. The method of claim 1, wherein said polymer is a homopolymer.

10. The method of claim 1, wherein said polymer is a heteropolymer.

11. The method of claim 1, further comprising incubating said compound under intein reaction conditions to produce said cyclic product.

12. The method of claim 1, wherein said polymer is synthetically made.

* * * * *